US012746274B2

(12) United States Patent
Xiang et al.

(10) Patent No.: US 12,746,274 B2
(45) Date of Patent: Sep. 29, 2026

(54) USE OF BMP9 IN COMBINATION WITH NK CELL AND PD-L1 ANTIBODY IN PREPARING MEDICAMENT FOR TREATING LIVER CANCER

(71) Applicants: Sun Yat-sen University, Guangzhou (CN); Sun Yat-sen University Cancer Center, Guangzhou (CN)

(72) Inventors: Tong Xiang, Guangzhou (CN); Jianchuan Xia, Guangzhou (CN); Yulong Han, Guangzhou (CN); Yao Zhu, Guangzhou (CN)

(73) Assignees: Sun Yat-sen University, Guangzhou (CN); Sun Yat-sen University Cancer Center, Guangzhou (CN)

( * ) Notice: Subject to any disclaimer, the term of this patent is extended or adjusted under 35 U.S.C. 154(b) by 711 days.

(21) Appl. No.: 18/195,381

(22) Filed: May 10, 2023

(65) Prior Publication Data

US 2023/0364190 A1 Nov. 16, 2023

(30) Foreign Application Priority Data

May 10, 2022 (CN) ......................... 202210502745.2

(51) Int. Cl.

| | |
|---|---|
| ***A61K 38/18*** | (2006.01) |
| ***A61K 35/17*** | (2025.01) |
| ***A61P 35/00*** | (2006.01) |
| ***C07K 16/28*** | (2006.01) |

(52) U.S. Cl.

CPC .......... *A61K 38/1875* (2013.01); *A61K 35/17* (2013.01); *A61P 35/00* (2018.01); *C07K 16/2896* (2013.01)

(58) Field of Classification Search

CPC ................ A61K 38/1875; A61K 35/17; A61K 2300/00; A61K 2039/505; A61K 49/223; A61P 35/00; C07K 16/2896; C07K 16/2827

See application file for complete search history.

(56) References Cited

U.S. PATENT DOCUMENTS

2016/0058907 A1* 3/2016 Kilway .................. A61K 38/18 524/588
2019/0153095 A1 5/2019 Matozaki et al.
2019/0177391 A1* 6/2019 Chen .................... C07K 14/575
2019/0365895 A1* 12/2019 Yeh ......................... A61P 35/00
2020/0148786 A1 5/2020 Kim et al.
2022/0305139 A1* 9/2022 Kim ................ A61K 39/39558

FOREIGN PATENT DOCUMENTS

| | | | | | |
|---|---|---|---|---|---|
| CN | 103463619 | A | 12/2013 | | |
| CN | 112410425 | A | 2/2021 | | |
| CN | 113117073 | A | 7/2021 | | |
| CN | 113574168 | A | 10/2021 | | |
| NZ | 590308 | A | 2/2012 | | |
| WO | WO-2007030534 | A2 * | 3/2007 | ............. | A61L 31/16 |
| WO | 2009084738 | A1 | 7/2009 | | |
| WO | 2021045485 | A1 | 3/2021 | | |

OTHER PUBLICATIONS

Sheyn_et_al_Gene_Therapy_2008 (Year: 2008).*
Han_et_al_Clin_Transl_Med._Published_May 2, 2023 (Year: 2023).*
Gong_et_al_IEEE_Trans_Biomed_Eng_2022 (Year: 2022).*
Kim_et_al_Pharmaceuticals_2020 (Year: 2020).*
Li_et_al_Cancer_Lett_2021 (Year: 2021).*
Yang_et_al_Front_Pharmacol._2019 (Year: 2019).*
Liu_et_al_Am_J_Transl_Res_2021 (Year: 2021).*
Jung_et_al_Oncotarget_2016_vol. 7_No. 45 (Year: 2016).*
Jae Woo Jung, et al., Bone morphogenetic protein-9 is a potent growth inhibitor of hepatocellular carcinoma and reduces the liver cancer stem cells population, Oncotarget, 2016, pp. 73754-73768, vol. 7, No. 45.
Claire Viallard, et al., BMP9 signaling promotes the normalization of tumor blood vessels, Oncogene, 2020, pp. 2996-3014, vol. 39, SpringerNature.
Liu Yang, et al., BMP9 Inhibit the Growth of MDA-MB-231 Breast Cancer Cells through PI3K/Akt Cell Signaling Pathway, Genomics and Applied Biology, 2016, pp. 2539-2544, vol. 35, No. 10.
Ma Cui, et al., Research progress of BMP9 and liver diseases, Chinese Pharmacological Bulletin, 2020, pp. 1045-1048, vol. 36, No. 8.

* cited by examiner

*Primary Examiner* — Catherine S Hibbert
(74) *Attorney, Agent, or Firm* — Bayramoglu Law Offices LLC

(57) ABSTRACT

A method of using BMP9 in combination with an NK cell and a PD-L1 antibody in preparing a medicament for treating liver cancer is provided. Specifically, BMP9 is loaded on a drug carrier microbubble to give a BMP9-carrying microbubble (MB-BMP9), and administered in combination with a natural killer cell (NK cell) and a programmed death-ligand 1 (PD-L1) antibody for treating hepatocellular carcinoma (HCC). The present invention can significantly enhance the efficacy of existing programmed death-ligand 1 (PD-L1) antibody therapies and significantly inhibit the growth of HCC cell graft tumors with significant efficacy.

2 Claims, 2 Drawing Sheets

A
Liver cancer cell
HepG2.2.15
+
MB
Liver cancer cell
HepG2.2.15
+
MB-BMP9
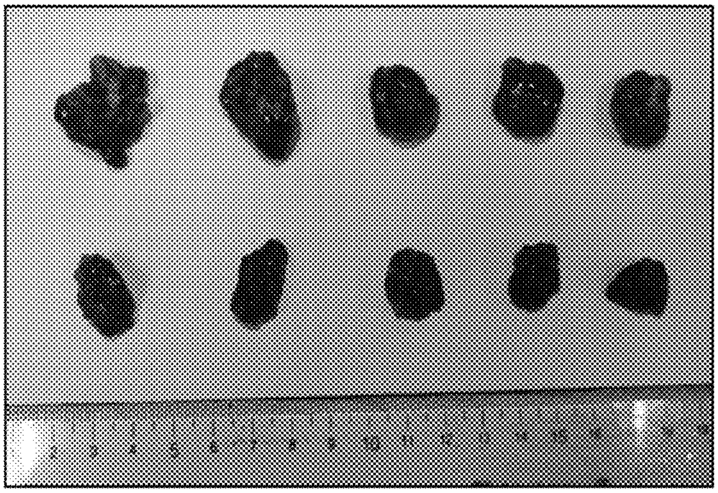
FIG. 1A
B
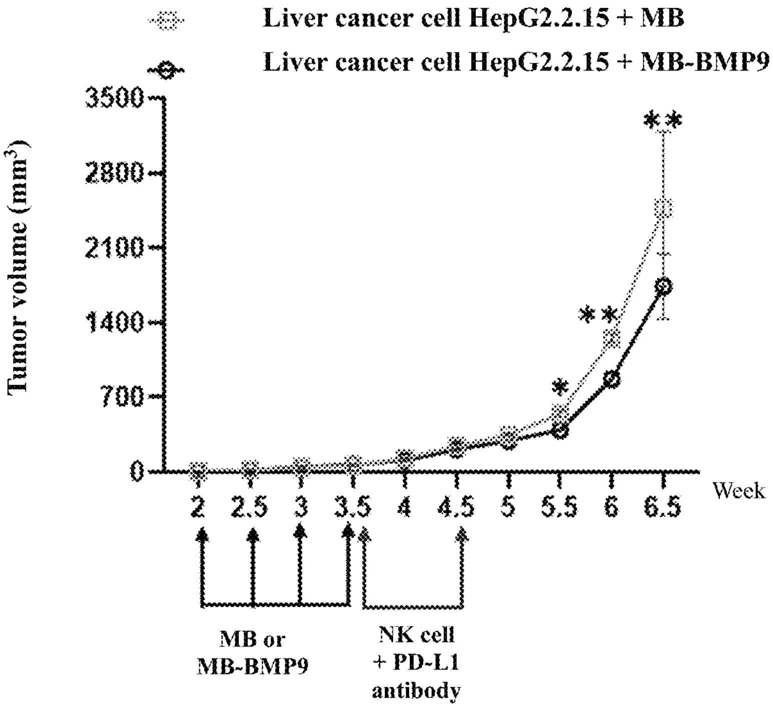

USE OF BMP9 IN COMBINATION WITH NK CELL AND PD-L1 ANTIBODY IN PREPARING MEDICAMENT FOR TREATING LIVER CANCER

CROSS REFERENCE TO THE RELATED APPLICATIONS

This application is based upon and claims priority to Chinese Patent Application 202210502745.2, filed on May 10, 2022, the entire contents of which are incorporated herein by reference.

TECHNICAL FIELD

The present invention relates to the technical field of pharmaceuticals, and particularly to use of bone morphogenetic protein 9 (BMP9) in combination with a natural killer cell (NK cell) and programmed death-ligand 1 (PD-L1) in preparing a medicament for treating a tumor.

BACKGROUND

Hepatocellular carcinoma (HCC) is the most common primary liver cancer and is expected to rank sixth among confirmed cancers and third in death of cancer globally. Among the risk factors of liver cancer, viral infection is the most critical factor, and chronic Hepatitis B Virus (HBV) infection is considered as the leading cause. Although early HCC can be cured by resection, liver transplantation, or ablation, most patients are suffering from an unresectable disease with a poor prognosis.

Programmed death-ligand 1 (PD-L1) is a 40-kDa type 1 transmembrane protein. PD-L1 (or B7-H1) is a member of the B7 family. having IgV and IgC-like regions, a transmembrane region, and a cytoplasmic region tail. PD-L1 interacts with a receptor PD1 on T cells thereof and plays an important role in the negative regulation of immune response. In normal conditions, the immune system responds to foreign antigens that accumulate in the lymph nodes or spleen, promoting the proliferation of antigen-specific cytotoxic T cells ($CD8^+$ T cell). Programmed cell death protein-1 (PD-1) binds to programmed death-ligand 1 (PD-L1) to conduct inhibitory signals and thus reduce the proliferation of $CD8^+$ T cells in lymph nodes. The molecule is overexpressed on certain tumor cells, and many studies showed that the molecule is associated with the immune escape mechanism of tumors. The microenvironment at the site of a tumor may induce a wide expression of PD-L1 on tumor cells, which is favorable for the development and growth of the tumor and induces the apoptosis of the anti-tumor T cells. PD-L1 can be the target of antibodies for resisting tumors, infections, and autoimmune diseases and the survival of organ grafts.

Based on the results of phase III trials, combinations of PD-L1 antibody (atezolizumab) with other therapeutics as the first-line treatment of unresectable HCC have been by the FDA, and a number of studies continue to delve into further improving the efficacy of PD-L1 antibody immunotherapies in patients with liver cancer. Although the PD-L1 antibody showed certain benefits in some unresectable HCC patients, and adverse events were generally acceptable, the response rate (about 20%) is unsatisfactory. Therefore, there's a need for new methods to improve the clinical benefit of PD-L1 antibody in treating HCC.

SUMMARY

The present invention is intended to provide use of BMP9 in combination with an NK cell and a PD-L1 antibody in improving the clinical efficacy for treating HCC. The combination exhibits more significant efficacy in treating HCC, suggesting that medicaments including BMP9 can be used in the prevention and treatment of HCC.

The present invention is intended to provide use of BMP9 in combination with an NK cell and a PD-L1 antibody in preparing a medicament for treating a tumor.

The present invention is also intended to provide a medicament for treating liver cancer.

The intentions of the present invention are realized by the following technical schemes:

The present invention provides use of BMP9 in combination with an NK cell and a PD-L1 antibody in preparing a medicament for treating a tumor.

Preferably, BMP9 is loaded on a drug carrier.

Preferably, the drug carrier is a microbubble, and MB-BMP9 is prepared.

Preferably, the NK cell is a group of lymphocytes derived from human cord blood.

Preferably, the PD-L1 antibody is an anti-human PD-L1 (B7-H1) antibody.

Preferably, treating the tumor refers to promoting tumor cell death or killing tumor cells, or inhibiting tumor cell growth.

Preferably, the tumor is HCC primary liver cancer.

Preferably, the tumor is HBV-positive HCC.

More preferably, the treating refers to treating HBV-positive HCC.

On this basis, the present invention further provides a medicament for treating liver cancer, including BMP9, an NK cell, and a PD-L1 antibody.

Preferably, the medicament includes MB-BMP9, the NK cell, and the PD-L1 antibody.

Preferably, the medicament may further include a pharmaceutically acceptable excipient.

In an immunodeficient NCG mouse subcutaneous tumor graft study, the comparison of groups with/without receiving BMP9 shows that BMP9 can significantly improve the tumor-killing capacity of NK cells combined with PD-L1 antibodies and inhibit the growth of the tumor.

MB-BMP9 used in embodiments of the present invention consists of a lipid bilayer shell, a bio-inert gas enclosed inside the shell, and BMP9 dispersed in the shell.

As an alternative embodiment, the lipid bilayer shell includes a phospholipid or a phospholipid derivative including: 1,2-distearoyl-sn-glycero-3-phosphocholine (DSPC), 1,2-distearoyl-sn-glycero-3-phosphoethanolamine (DSPE)-polyethylene glycol 2000 (PEG2000), and stearic acid-modified branched polyethylenimine-600 (Stearic-PEI600).

Preferably, the inert gas is perfluoropropane.

The present invention further provides a method for preparing MB-BMP9, including:

S1: dissolving 1,2-distearoyl-sn-glycero-3-phosphocholine (DSPC), 1,2-distearoyl-sn-glycero-3-phosphoethanolamine (DSPE)-polyethylene glycol 2000 (PEG2000), and stearic acid-modified branched polyethylenimine-600 (Stearic-PEI600) in an organic solvent, and stirring for half an hour to give a phospholipid suspension;

S2: uniformly mixing the phospholipid suspension, and removing the organic solvent;

S3: adding PBS, and incubating in a 40-80° C. water bath for 10-30 min;

S4: shaking the solution after the water bath for 30-60 s in a bio-inert gas atmosphere, centrifuging to give an ultrasound microbubble, and washing to remove the phospholipid that does not form the microbubble; and S5: adding BMP9 into the washed microbubble, and incubating for 1.5-2.5 h at room temperature to give a drug-carrying microbubble.

In S1, the mass ratio of 1,2-distearoyl-sn-glycero-3-phosphocholine (DSPC), 1,2-distearoyl-sn-glycero-3-phosphoethanolamine (DSPE)-polyethylene glycol 2000 (PEG2000), and stearic acid-modified branched polyethylenimine-600 (Stearic-PEI600) is (75-90):9:9. Preferably, the mass ratio of the three substances is 82:9:9.

In S1 and S2, the organic solvent is a mixture of chloroform and methanol in a volume ratio of (7-11):1 (preferably, the volume ratio of chloroform to methanol is 9:1).

In S4, the bio-inert gas is perfluoropropane.

In S4, the centrifugation condition is 200-500 g/min for 2-10 min, preferably 400 g/min for 4 min.

In S4 and S5, the method for washing is centrifugal floating.

In S5, the amount ratio of BMP9 to the microbubble is (10-30 μg):$10^8$, preferably 20 μg:$10^8$.

The present invention possesses the following beneficial effects:

The present invention provides use of BMP9 in combination with an NK cell and a PD-L1 antibody in preparing a medicament for treating a tumor. By using the combination of BMP9 with the NK cell and the PD-L1 antibody in treating HCC, the present invention can significantly enhance the efficacy of existing programmed death-ligand 1 (PD-L1) antibody therapies and significantly inhibit the growth of HCC cell graft tumors with significant efficacy, suggesting that medicaments including BMP9 can be used in the prevention and treatment of HCC.

BRIEF DESCRIPTION OF THE DRAWINGS

FIGS. 1A-1B show the effect of MB-BMP9 or blank microbubble MB in combination with NK cells and PD-L1 antibody on the size of HBV-positive HCC cell grafts; in FIGS. 1A-1B, FIG. 1A shows a photograph of tumors collected from mice 6.5 weeks after the tumor grafting; FIG. 1B shows the measurements of tumor graft size by a vernier caliper every 0.5 weeks in mice receiving MB-BMP9 or blank microbubble MB in weeks 2 to 3.5 and NK cells and PD-L1 antibody in weeks 3.5 to 4.5.

FIG. 2A shows the expressions in NK cells (marked with CD56) and activated NK cells (marked with CD69) in mouse tumor grafts by immunohistochemistry; FIG. 2B shows the numbers of NK cells (marked with CD56) and activated NK cells (marked with CD69) in the mouse tumor grafts calculated under a microscope in 200-fold magnification.

DETAILED DESCRIPTION OF THE EMBODIMENTS

Figure 2A:
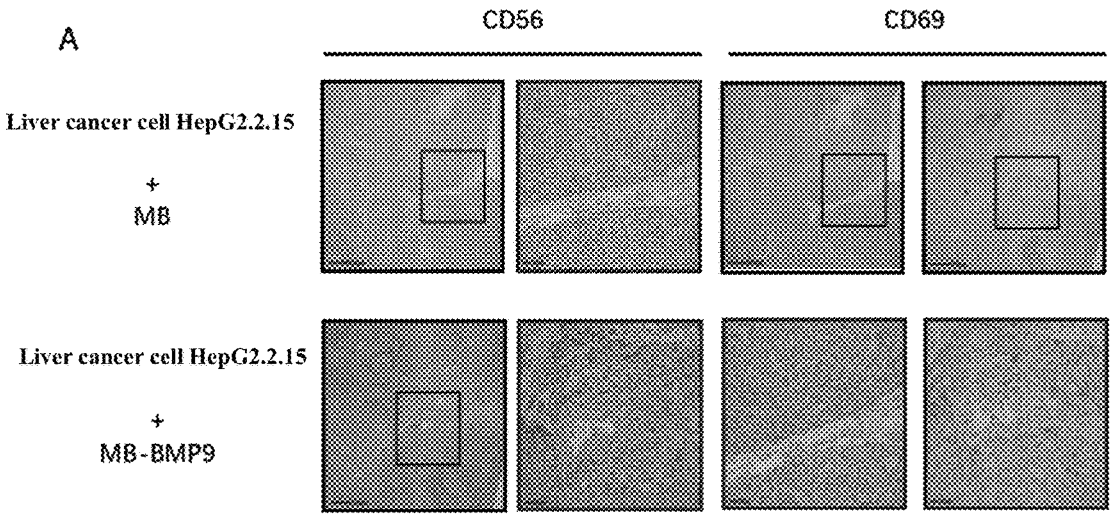
FIGS. 2A-2B show the effect of MB-BMP9 or blank microbubble MB in combination with NK cells and PD-L1 antibody on the number and viability of NK cells in HBV-positive HCC cell grafts; in FIGS. 2A-2B.

The present invention is further illustrated with reference to the drawings and specific embodiments, which are, however, not intended to limit the present invention by any means. Unless otherwise indicated, the reagents, methods, and instruments used in the present invention are those conventional in the art.

Unless otherwise indicated, the reagents and materials used in the following examples are commercially available.

Through years of efforts, the team of the inventors found that HBV infection is considered as the leading cause of HCC. Therefore, the following embodiments are presented by way of examples of HBV-positive HCC.

Example 1

Preparation of MB-BMP9

S1: 82 parts of 1,2-distearoyl-sn-glycero-3-phosphocholine (DSPC), 9 parts of 1,2-distearoyl-sn-glycero-3-phosphoethanolamine (DSPE)-polyethylene glycol 2000 (PEG2000), and 9 parts of stearic acid-modified branched polyethylenimine-600 (Stearic-PEI600) were dissolved in a mixture of 18 mL of chloroform and 2 mL of methanol; the mixture was stirred with a magnetic stirrer for half an hour.

S2: The phospholipid suspension was mixed well, and the organic solvent was removed on a high-speed rotary evaporator in vacuum at 60° C. for 2 hours; the remaining organic solvent was further removed by drying in vacuum for 2 hours.

S3: 5 mL of PBS was added and the mixture was incubated in a 60° C. water bath for 15 min.

S4: The solution was transferred into vials; the headspace of the vials was filled with bio-inert gas perfluoropropane; the vials were shaken for 40 s before the solutions were centrifuged at 400 g/min for 4 min to give microbubbles; the microbubbles were washed 4 times by centrifugal floating to remove the phospholipid that did not form microbubbles.

S5: 20 μg of BMP9 was added into $10^8$ washed microbubbles: the mixture was gently shaken and incubated for 1.5 h at room temperature, and washed 4 times by centrifugal floating to give drug-carrying microbubbles.

Example 2

Preparation of MB-BMP9

S1: 75 parts of 1,2-distearoyl-sn-glycero-3-phosphocholine (DSPC), 9 parts of 1,2-distearoyl-sn-glycero-3-phosphoethanolamine (DSPE)-polyethylene glycol 2000 (PEG2000), and 9 parts of stearic acid-modified branched polyethylenimine-600 (Stearic-PEI600) were dissolved in a mixture of 14 mL of chloroform and 2 mL of methanol; the mixture was stirred with a magnetic stirrer for half an hour.

S2: The phospholipid suspension was mixed well, and the organic solvent was removed on a high-speed rotary evaporator in vacuum at 60° C. for 2 hours; the remaining organic solvent was further removed by drying in vacuum for 2 hours.

S3: 5 mL of PBS was added and the mixture was incubated in an 80° C. water bath for 10 min.

S4: The solution was transferred into vials; the headspace of the vials was filled with bio-inert gas perfluoropropane; the vials were shaken for 30 s before the solutions were centrifuged at 200 g/min for 10 min to give microbubbles; the microbubbles were washed 4 times by centrifugal floating to remove the phospholipid that did not form microbubbles.

S5: 15 μg of BMP9 was added into $10^8$ washed microbubbles: the mixture was gently shaken and incubated for 1.5 h at room temperature, and washed 4 times by centrifugal floating to give drug-carrying microbubbles.

Example 3

Preparation of MB-BMP9

S1: 80 parts of 1,2-distearoyl-sn-glycero-3-phosphocholine (DSPC), 9 parts of 1,2-distearoyl-sn-glycero-3-phosphoethanolamine (DSPE)-polyethylene glycol 2000 (PEG2000), and 9 parts of stearic acid-modified branched polyethylenimine-600 (Stearic-PEI600) were dissolved in a mixture of 16 mL of chloroform and 2 mL of methanol; the mixture was stirred with a magnetic stirrer for half an hour.

S2: The phospholipid suspension was mixed well, and the organic solvent was removed on a high-speed rotary evaporator in vacuum at 60° C. for 2 hours; the remaining organic solvent was further removed by drying in vacuum for 2 hours.

S3: 5 mL of PBS was added and the mixture was incubated in a 50° C. water bath for 20 min.

S4: The solution was transferred into vials; the headspace of the vials was filled with bio-inert gas perfluoropropane; the vials were shaken for 50 s before the solutions were centrifuged at 300 g/min for 6 min to give microbubbles; the microbubbles were washed 4 times by centrifugal floating to remove the phospholipid that did not form microbubbles.

S5: 30 μg of BMP9 was added into $10^8$ washed microbubbles: the mixture was gently shaken and incubated for 2.0 h at room temperature, and washed 4 times by centrifugal floating to give drug-carrying microbubbles.

Example 4

Preparation of MB-BMP9

S1: 85 parts of 1,2-distearoyl-sn-glycero-3-phosphocholine (DSPC), 9 parts of 1,2-distearoyl-sn-glycero-3-phosphoethanolamine (DSPE)-polyethylene glycol 2000 (PEG2000), and 9 parts of stearic acid-modified branched polyethylenimine-600 (Stearic-PEI600) were dissolved in a mixture of 20 mL of chloroform and 2 mL of methanol; the mixture was stirred with a magnetic stirrer for half an hour.

S2: The phospholipid suspension was mixed well, and the organic solvent was removed on a high-speed rotary evaporator in vacuum at 60° C. for 2 hours; the remaining organic solvent was further removed by drying in vacuum for 2 hours.

S3: 5 mL of PBS was added and the mixture was incubated in a 70° C. water bath for 25 min.

S4: The solution was transferred into vials; the headspace of the vials was filled with bio-inert gas perfluoropropane; the vials were shaken for 60 s before the solutions were centrifuged at 500 g/min for 8 min to give microbubbles; the microbubbles were washed 4 times by centrifugal floating to remove the phospholipid that did not form microbubbles.

S5: 10 μg of BMP9 was added into $10^8$ washed microbubbles: the mixture was gently shaken and incubated for 2.0 h at room temperature, and washed 4 times by centrifugal floating to give drug-carrying microbubbles.

Example 5

Preparation of MB-BMP9

S1: 90 parts of 1,2-distearoyl-sn-glycero-3-phosphocholine (DSPC), 9 parts of 1,2-distearoyl-sn-glycero-3-phosphoethanolamine (DSPE)-polyethylene glycol 2000 (PEG2000), and 9 parts of stearic acid-modified branched polyethylenimine-600 (Stearic-PEI600) were dissolved in a mixture of 22 mL of chloroform and 2 mL of methanol; the mixture was stirred with a magnetic stirrer for half an hour.

S2: The phospholipid suspension was mixed well, and the organic solvent was removed on a high-speed rotary evaporator in vacuum at 60° C. for 2 hours; the remaining organic solvent was further removed by drying in vacuum for 2 hours.

S3: 5 mL of PBS was added and the mixture was incubated in an 80° C. water bath for 20 min.

S4: The solution was transferred into vials; the headspace of the vials was filled with bio-inert gas perfluoropropane; the vials were shaken for 60 s before the solutions were centrifuged at 500 g/min for 5 min to give microbubbles; the microbubbles were washed 4 times by centrifugal floating to remove the phospholipid that did not form microbubbles.

S5: 20 μg of BMP9 was added into $10^8$ washed microbubbles: the mixture was gently shaken and incubated for 2.5 h at room temperature, and washed 4 times by centrifugal floating to give drug-carrying microbubbles.

Example 6

Effect of MB-BMP9 in Combination with NK Cells and PD-L1 Antibody on HBV-positive HCC Cell Tumor Graft 1. Materials (1) MB-BMP9 prepared in Example 1.

Blank microbubbles MB (i.e., microbubbles obtained in S4) were prepared according to the method in Example 1.

(2) NK cells: human cord blood-derived NK cells.

(3) PD-L1 antibody: anti-human PD-L1 (B7-H1) antibody.

(4) Cancer cells: HBV-positive HCC cells (HepG2.2.15).

(5) Commercially available immunodeficient NCG mice.

2. Grouping)

MB+NK cells+PD-L1 antibody group: blank microbubbles were administered through the tail vein, and the HBV-positive HCC cell tumor graft was ultrasonicated; NK cells and the PD-L1 antibody were administered through the tail vein.

(2) MB-BMP9+NK cells+PD-L1 antibody group: MB-BMP9 was administered through the tail vein, and the HBV-positive HCC cell tumor graft was ultrasonicated; NK cells and the PD-L1 antibody were administered through the tail vein.

3. Immunodeficient NCG Mice Subcutaneous Tumor Graft Study for Detecting HBV-Positive HCC Cell Tumor Grafts in Various Groups S1: a. HBV-positive HCC cells (HepG2.2.15) were grafted subcutaneously at the axillary fossa into 8 NSG mice aged 3-4 weeks at an amount of $2.5\times10^6$.

b. The mice were randomied into 2 groups: an MB+NK cell+PD-L1 antibody group and MB-BMP9+NK cell+PD-L1 antibody group.

S2: a. At week 2 after the tumor grafting, 20 ng of MB was administered to each mouse in the MB+NK cell+PD-L1 antibody group once every 3 days through the tail vein, and the tumor was ultrasonicated 4 times continuously; 20 ng of MB-BMP9 was administered to each mouse in the MB-BMP9+NK cell+PD-L1 antibody group once every 3 days through the tail vein, and the tumor was ultrasonicated 4 times continuously.

b. At weeks 3.5 and 4.5, the two groups were administered once with $1.0\times10^7$ NK cells through the tail vein and once with 0.2 mg of the PD-L1 antibody intraperitoneally; the mice were then given maintenance therapy with IL-2 ($10^4$ units/mouse/3 days).

S3: The tumor size was measured every 3 days with a vernier caliper, and differences in tumor growth were compared between the groups.

S4: after 6.5 weeks, the mice were sacrificed and the tumor tissues were collected and photographed. The expression of the NK cell marker (CD56) and the activated NK cell marker (CD69) were examined by immunohistochemistry.

4. Results

The experimental results are shown in FIGS. 1A-1B and FIGS. 2A-2B. FIGS. 1A-1B show the effect of MB-BMP9 or blank microbubble MB in combination with NK cells and PD-L1 antibody on the size of HBV-positive HCC cell grafts; where FIG. 1A shows a photograph of tumors collected from mice 6.5 weeks after the tumor grafting; FIG. 1B shows the measurements of tumor graft size by a vernier caliper every 0.5 weeks in mice receiving MB-BMP9 or blank microbubble MB in weeks 2 to 3.5 and NK cells and PD-L1 antibody in weeks 3.5 to 4.5. * indicates a significant difference between the results from the two groups, $P<0.05$; ** indicates a significant difference between the results from the two groups, $P<0.01$.

Figure 2B:
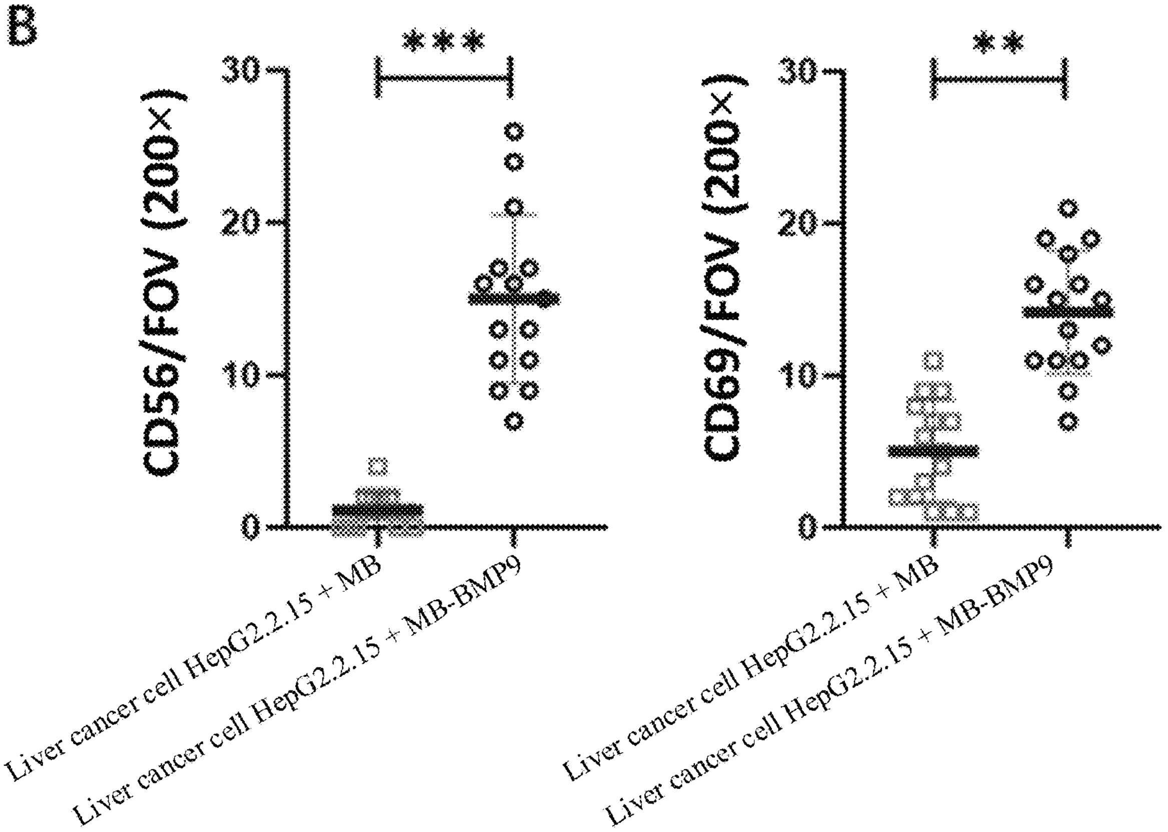

FIGS. 2A-2B show the effect of MB-BMP9 or blank microbubble MB in combination with NK cells and PD-L1 antibody on the number and viability of NK cells in HBV-positive HCC cell grafts; where FIG. 2A show the expressions in NK cells (marked with CD56) and activated NK cells (marked with CD69) in mouse tumor grafts by immunohistochemistry; FIG. 2B show the numbers of NK cells (marked with CD56) and activated NK cells (marked with CD69) in the mouse tumor grafts calculated under a microscope in 200-fold magnification.  indicates a significant difference between the results from the two groups, $P<0.01$; * indicates a significant difference between the results from the two groups, $P<0.001$.

As shown in FIGS. 1A-1B and FIGS. 2A-2B, MB-BMP9 in combination with NK cells and PD-L1 antibody has a significantly enhanced ability to kill tumors and inhibit the growth of tumors.

As shown in FIGS. 2A-2B, the immunohistochemical results show that MB-BMP9 is capable of increasing the number of NK cells and activated NK cells in HCC tumor tissues.

5. Analysis of Results

The addition of BMP9 to the existing combination therapy of NK cells and the PD-L1 antibody for treating HCC can significantly enhance the efficacy of the NK cells and PD-L1 antibody in treating HCC. The combination of BMP9 with NK cells and PD-L1 antibody for treating HCC can significantly inhibit the growth of HCC cell graft tumors with significant efficacy.

The above embodiments are preferred embodiments of the present invention. However, the present invention is not limited to the above embodiments, and any other changes, modifications, substitutions, combinations, and simplifications which do not depart from the spirit and principle of the present invention should be construed as equivalents thereof and included in the scope of the present invention.

What is claimed is:

1. A method for treating HBV-positive liver cancer comprising administering a BMP9 in combination with an NK cell and a PD-L1 antibody to a subject in need thereof, wherein the BMP9 is loaded on a drug-carrying microbubble (MB-BMP9);

and the MB-BMP9 is prepared by the following steps:

S1: dissolving 1,2-distearoyl-sn-glycero-3-phosphocholine (DSPC), 1,2-distearoyl-sn-glycero-3-phosphoethanolamine (DSPE)-polyethylene glycol 2000 (PEG2000), and stearic acid-modified branched polyethylenimine-600 (Stearic-PEI600) in an organic solvent to obtain a first resulting mixture, and stirring the first resulting mixture for half an hour to give a phospholipid suspension;

S2: uniformly mixing the phospholipid suspension, and removing the organic solvent from the phospholipid suspension to obtain a second resulting mixture;

S3: adding phosphate-buffered saline (PBS) in the second resulting mixture to obtain a resulting solution, and incubating the resulting solution in a 60° C. water bath for 15 min to obtain an incubated solution;

S4: shaking the incubated solution for 40 s in a bio-inert gas atmosphere, centrifuging the incubated solution to give an ultrasound microbubble, and washing the ultrasound microbubble to remove a phospholipid not forming the ultrasound microbubble; and S5: adding the BMP9 into a washed microbubble to obtain a third resulting mixture, and incubating the third resulting mixture for 1.5 h at room temperature to give the MB-BMP9; wherein in S1, a mass ratio of the DSPC, the DSPE-PEG2000, and the Stearic-PEI600 is 82:9:9;

in S1 and S2, the organic solvent is a mixture of chloroform and methanol in a volume ratio of 9:1;

in S4, the bio-inert gas atmosphere is perfluoropropane;

in S4, a centrifugation condition is 400 g/min for 4 min;

in S4, a method for washing is centrifugal floating; and in S5, an amount ratio of the BMP9 to the washed microbubble is 20 μg:$10^8$.

2. The method according to claim 1, wherein the BMP9 in combination with the NK cell and the PD-L1 antibody is effective for promoting a tumor cell death or killing tumor cells.

* * * * *